United States Patent
Tsubota et al.

(10) Patent No.: US 10,908,071 B2
(45) Date of Patent: Feb. 2, 2021

(54) ENVIRONMENTAL MEASUREMENT SYSTEM AND NON-TRANSITORY COMPUTER READABLE MEDIUM

(71) Applicant: FUJI XEROX CO., LTD., Tokyo (JP)

(72) Inventors: Hirokazu Tsubota, Kanagawa (JP);
Kunitoshi Yamamoto, Kanagawa (JP);
Hajime Kajiyama, Kanagawa (JP);
Toshihiko Shibusawa, Kanagawa (JP);
Masatoshi Maruo, Kanagawa (JP);
Yasuharu Sakurai, Kanagawa (JP);
Mariko Miyazaki, Kanagawa (JP);
Hideki Fujimoto, Kanagawa (JP);
Naoya Ogata, Kanagawa (JP); Tetsuya Kobayashi, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 233 days.

(21) Appl. No.: 15/715,641

(22) Filed: Sep. 26, 2017

(65) Prior Publication Data
US 2018/0259443 A1    Sep. 13, 2018

(30) Foreign Application Priority Data

Mar. 7, 2017  (JP) ................................ 2017-042496

(51) Int. Cl.
*G01N 21/01*    (2006.01)
*G01N 33/00*    (2006.01)
*G01K 1/02*    (2006.01)

(52) U.S. Cl.
CPC ............. *G01N 21/01* (2013.01); *G01K 1/024* (2013.01); *G01N 33/0075* (2013.01)

(58) Field of Classification Search
CPC .... G01N 21/01; G01N 33/0075; G01K 1/024; G01K 2213/00; G01W 1/02; G01W 2001/006; G01W 2203/00
(Continued)

(56) References Cited

U.S. PATENT DOCUMENTS

| 4,652,122 A | * | 3/1987 | Zincone | .................. | G01S 17/95 |
| | | | | | 356/28.5 |
| 2006/0184274 A1 | * | 8/2006 | Sakai | ................... | G05D 1/0246 |
| | | | | | 700/245 |

(Continued)

FOREIGN PATENT DOCUMENTS

| JP | H01-250762 A | 10/1989 |
| JP | 2005-118953 A | 5/2005 |

(Continued)

OTHER PUBLICATIONS

Dec. 1, 2020 Office Action issued in Japanese Patent Application No. 2017-042496.

*Primary Examiner* — Benjamin R Schmitt
(74) *Attorney, Agent, or Firm* — Oliff PLC

(57) ABSTRACT

An environmental measurement system includes a moving apparatus and an output unit. The moving apparatus includes an acquiring unit that acquires information on environmental factors, and the moving apparatus is capable of autonomously moving in a predefined region. The output unit outputs an environmental factor distribution in the region, and the environmental factor distribution has been calculated on the basis of the information on environmental factors acquired by the moving apparatus and location information of the moving apparatus at the time the information on environmental factors was acquired.

11 Claims, 12 Drawing Sheets

(58) Field of Classification Search
USPC .............................. 73/178 R, 170.28, 865.8
See application file for complete search history.

(56) References Cited

U.S. PATENT DOCUMENTS

| | | | | |
|---|---|---|---|---|
| 2012/0271491 A1* | 10/2012 | Spata | ...................... | G01W 1/00 |
| | | | | 701/3 |
| 2015/0242889 A1* | 8/2015 | Zamer | ................ | G06Q 30/0252 |
| | | | | 705/14.5 |
| 2017/0090070 A1* | 3/2017 | Root | ....................... | G01W 1/08 |

FOREIGN PATENT DOCUMENTS

| | | |
|---|---|---|
| JP | 2005-271781 A | 10/2005 |
| JP | 2006-000999 A | 1/2006 |
| JP | 2007-32954 A | 2/2007 |
| JP | 2011-187030 A | 9/2011 |
| JP | 2017-509968 A | 4/2017 |
| WO | 2015/118739 A1 | 8/2015 |

* cited by examiner

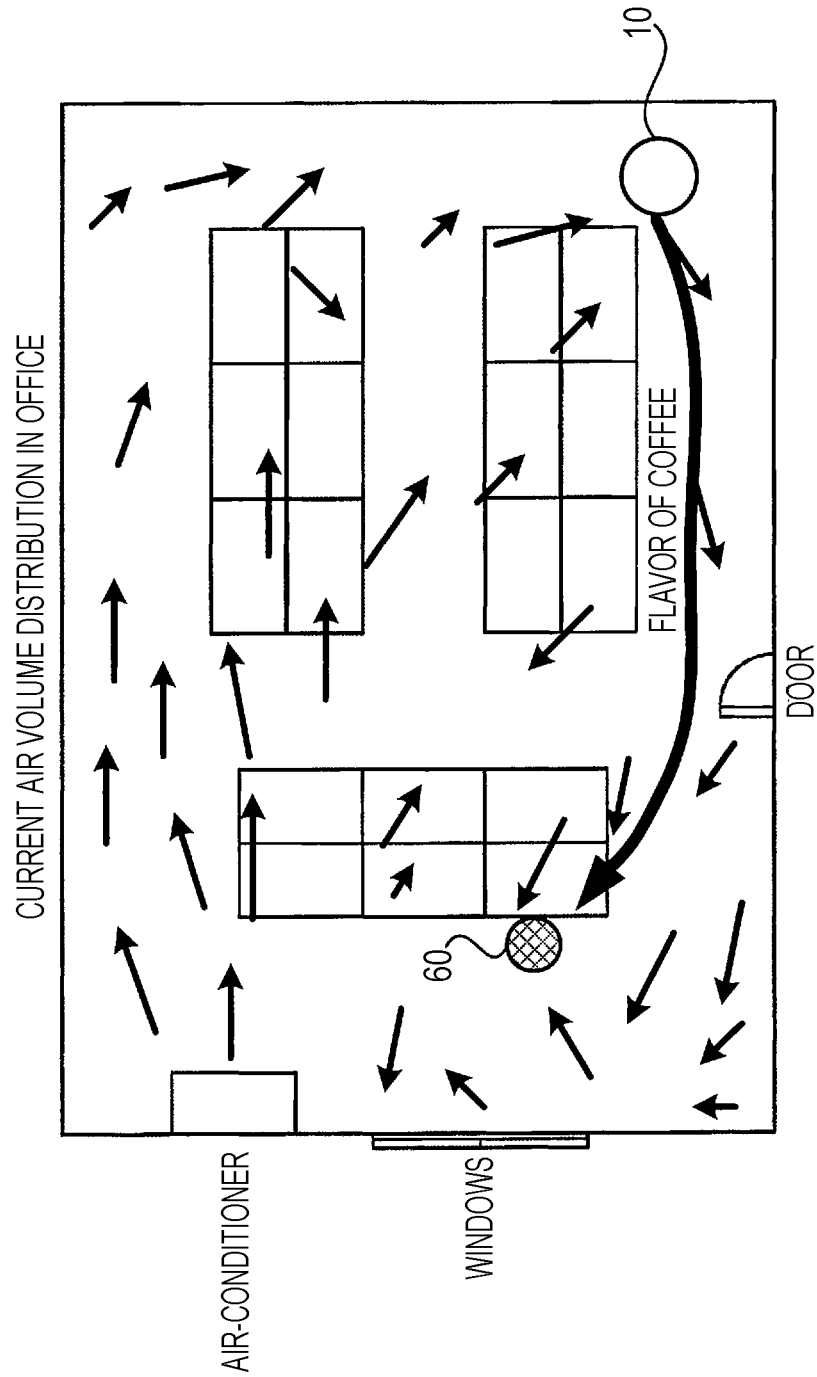

US 10,908,071 B2

ENVIRONMENTAL MEASUREMENT SYSTEM AND NON-TRANSITORY COMPUTER READABLE MEDIUM

CROSS-REFERENCE TO RELATED APPLICATIONS

This application is based on and claims priority under 35 USC 119 from Japanese Patent Application No. 2017-042496 filed Mar. 7, 2017.

BACKGROUND

Technical Field

The present invention relates to an environmental measurement system and a non-transitory computer readable medium.

SUMMARY

According to an aspect of the invention, there is provided an environmental measurement system including a moving apparatus and an output unit. The moving apparatus includes an acquiring unit that acquires information on environmental factors, and the moving apparatus is capable of autonomously moving in a predefined region. The output unit outputs an environmental factor distribution in the region, and the environmental factor distribution has been calculated on the basis of the information on environmental factors acquired by the moving apparatus and location information of the moving apparatus at the time the information on environmental factors was acquired.

BRIEF DESCRIPTION OF THE DRAWINGS

An exemplary embodiment of the present invention will be described in detail based on the following figures, wherein:

FIG. 12 illustrates a state in which, in a case of selling coffee by using the moving apparatus, the moving apparatus is caused to wait at the upstream of a user who often buys a coffee so that the flavor of coffee is delivered to the user.

DETAILED DESCRIPTION

Now, an exemplary embodiment of the present invention will be described in detail with reference to the drawings.

Figure 1:
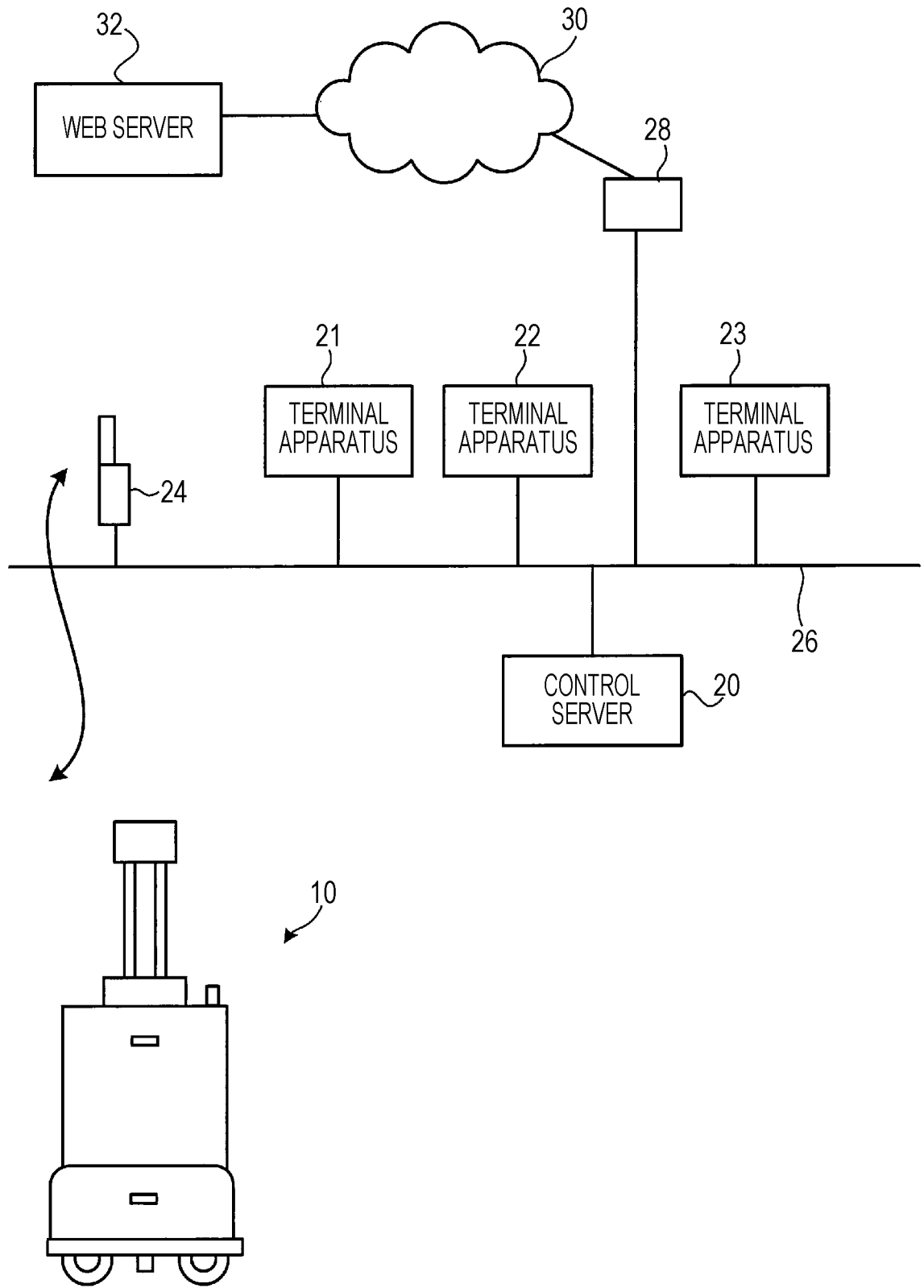
FIG. 1 is a system diagram illustrating a configuration of an environmental measurement system according to the exemplary embodiment of the present invention.

FIG. 1 is a system diagram illustrating a configuration of an environmental measurement system according to the exemplary embodiment of the present invention.

As illustrated in FIG. 1, the environmental measurement system according to the exemplary embodiment of the present invention includes, for example, a moving apparatus 10 that is a robot capable of autonomously moving in a predefined region such as an office. The moving apparatus 10 includes a moving unit for moving in the office so as to freely move in the office by using the moving unit.

Here, a case will be described below in which a service is provided by the moving apparatus 10 moving in an office. Thus, the predefined region is the office in which the moving apparatus 10 moves. However, if the region in which the moving apparatus 10 moves in order to provide a service is a shop such as a restaurant or a coffee shop, an area in the shop is the predefined region.

Note that the exemplary embodiment will be described on the assumption that the moving apparatus 10 measures environmental factors such as the temperature, the humidity, and the air volume in the office. However, the moving apparatus 10 may implement a service of providing foods and beverages including coffee, a printing service, and the like, or may implement any two or more services above.

The moving apparatus 10 is connected to a local network 26 through a wireless local area network (LAN) terminal 24. The local network 26 is connected to terminal apparatuses 21 to 23, such as personal computers, and a control server 20 for controlling the operation of the moving apparatus 10. In addition, the local network 26 is connected to an internet 30 through a router 28, and the control server 20 is accessible to a web server 32 through the internet 30.

Figure 2:
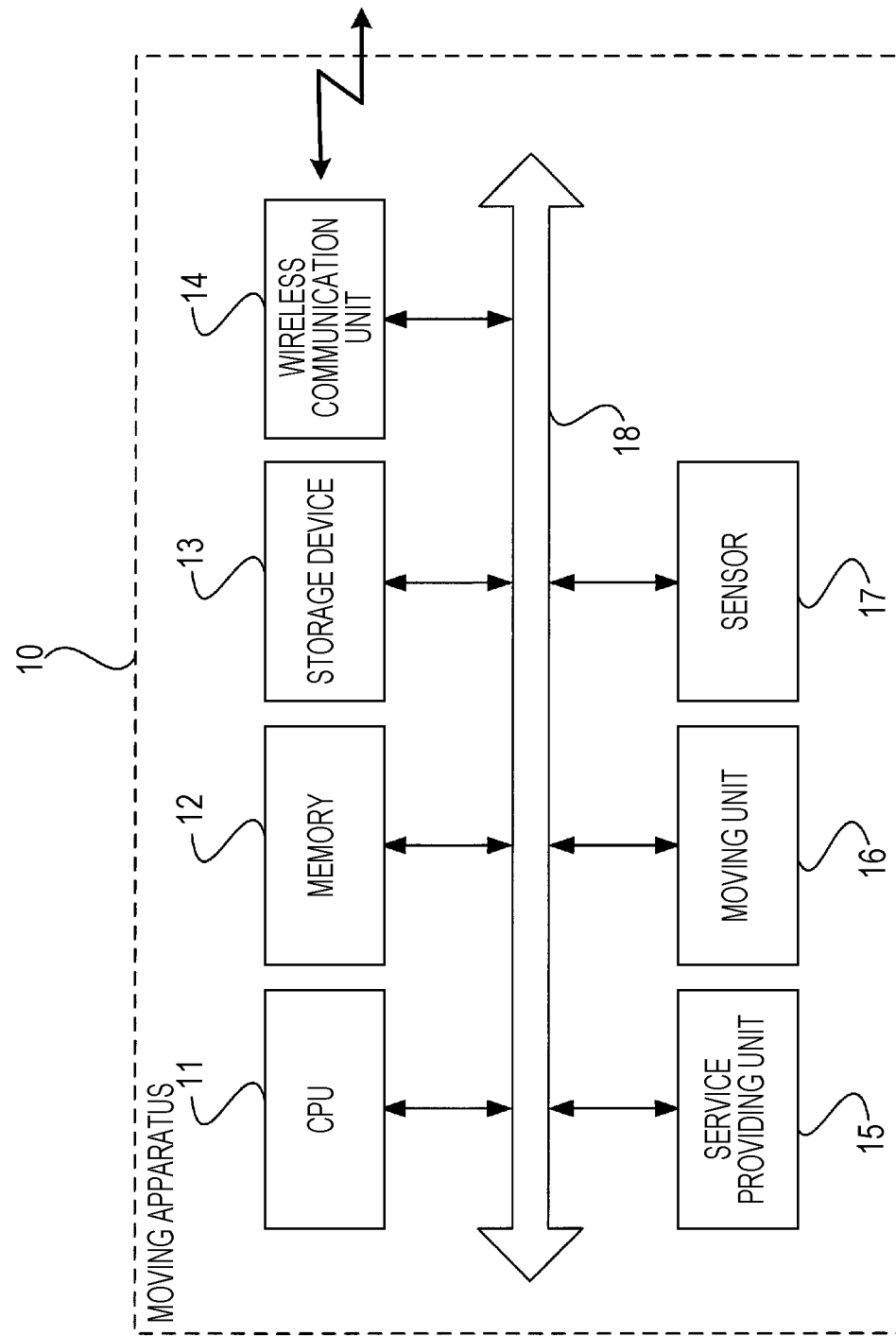
FIG. 2 is a block diagram illustrating a hardware configuration of a moving apparatus in the environmental measurement system according to the exemplary embodiment of the present invention.

Next, FIG. 2 illustrates a hardware configuration of the moving apparatus 10 in the environmental measurement system according to the exemplary embodiment.

As illustrated in FIG. 2, the moving apparatus 10 includes a central processing unit (CPU) 11, a memory 12, a storage device 13 such as a hard disk drive (HDD), a wireless communication unit 14 that transmits and receives data to and from the wireless LAN terminal 24 through a wireless network, a service providing unit 15 that is used when providing a food-and-beverage service or a printing service, a moving unit 16 for moving in the office, and a sensor 17 for measuring various environmental factors and for detecting the ambient conditions, obstacles, and the like. These components are connected to one another through a control bus 18.

The CPU 11 performs predetermined processes on the basis of control programs stored in the memory 12 or the storage device 13 and controls the operation of the moving apparatus 10. Note that the exemplary embodiment describes the CPU 11 as a unit that reads and executes the control programs stored in the memory 12 or the storage device 13. However, the programs may be stored in a storage medium such as a compact-disc read-only-memory (CD-ROM) and may be provided to the CPU 11.

As the sensor 17 for acquiring information on environmental factors, for example, a temperature sensor, a humidity sensor, an air volume sensor, an odor sensor, a noise (sound volume) sensor, a light intensity sensor, or the like is used.

Specifically, as the temperature sensor, a sensor that measures temperature information by using a change in the resistance value of a semiconductor may be used. In addition, as the humidity sensor, a sensor that measures humidity information by using a change in electrical characteristics due to moisture absorption/desorption on the sensor, such as a sensor of a polymer resistive type, a polymer capacitive type, or aluminum-oxide capacitive type, may be used.

The air volume sensor may be a sensor that acquires, as information on environmental factors, airflow direction information and airflow speed information in an open space on the basis of the direction and speed of the movement of fine substances in the open space detected by radiating a laser into the open space. When calculating the airflow direction information and airflow speed information, in consideration of the running speed of the moving apparatus 10, the detected airflow direction information and airflow speed information are corrected by using the running speed of the moving apparatus 10 to calculate the actual airflow direction information and airflow speed information.

Note that the moving apparatus 10 according to the exemplary embodiment includes a laser rangefinder for determining the shapes of surrounding objects to determine the location of the moving apparatus 10 or for detecting surrounding obstacles to stop the movement of the moving apparatus 10, for example. By using a laser radiated from the laser rangefinder, the airflow direction information and airflow speed information at a corresponding point may be acquired by the above method.

The airflow direction information and airflow speed information are acquired as information of environmental factors by such a method, and thereby an upstream airflow direction and an upstream airflow speed at a point away from the moving apparatus 10 are measured.

In addition, as the odor sensor, for example, an indium-oxide-based hot wire semiconductor sensor that detects an odorous component may be used.

As the noise sensor, a sensor that detects a current density generated by an electromotive force by using a sound collecting unit such as a microphone may be used.

As the light intensity sensor, a sensor that detects a current density generated by an electromotive force of a power generating element in which p-channel and n-channel semiconductors, for example, are combined may be used.

Figure 3:
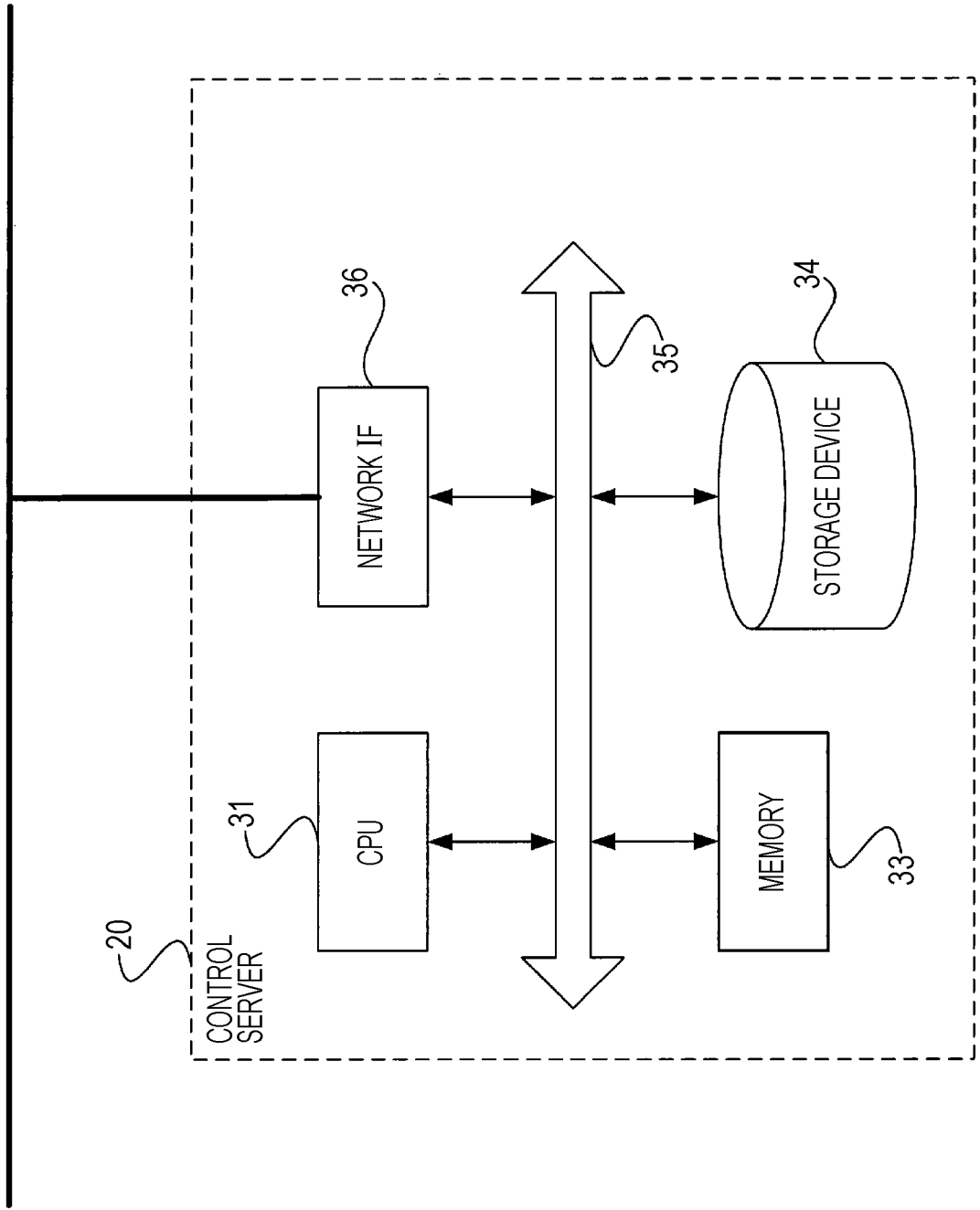
FIG. 3 illustrates a hardware configuration of a control server in the environmental measurement system according to the exemplary embodiment of the present invention.

Next, FIG. 3 illustrates a hardware configuration of the control server 20 in the environmental measurement system according to the exemplary embodiment.

As illustrated in FIG. 3, the control server 20 includes a CPU 31, a network interface (IF) 36, a memory 33, and a storage device 34, which are connected to one another through a control bus 35. The CPU 31 performs predetermined processes on the basis of control programs stored in the memory 33 or the storage device 34 and controls the operation of the control server 20. The memory 33 stores control programs. The storage device 34 stores host control programs, information on various environmental factors acquired by the moving apparatus 10, map information such as the layout of the office in which the moving apparatus 10 moves, and the like.

The memory includes a volatile memory and a non-volatile memory. The non-volatile memory (Flash-ROM) stores programs, and the volatile memory (Dynamic-RAM) is used as a work memory. Although a storage device such as an HDD may be used, a DRAM is usually used for its shorter access time.

The control server 20 is connected to the local network 26 through the network IF 32, thereby being capable of transmitting and receiving data to and from the wireless LAN terminal 24 and the terminal apparatuses 21 to 23 and accessing the web server 32 through the internet 30.

Figure 4:
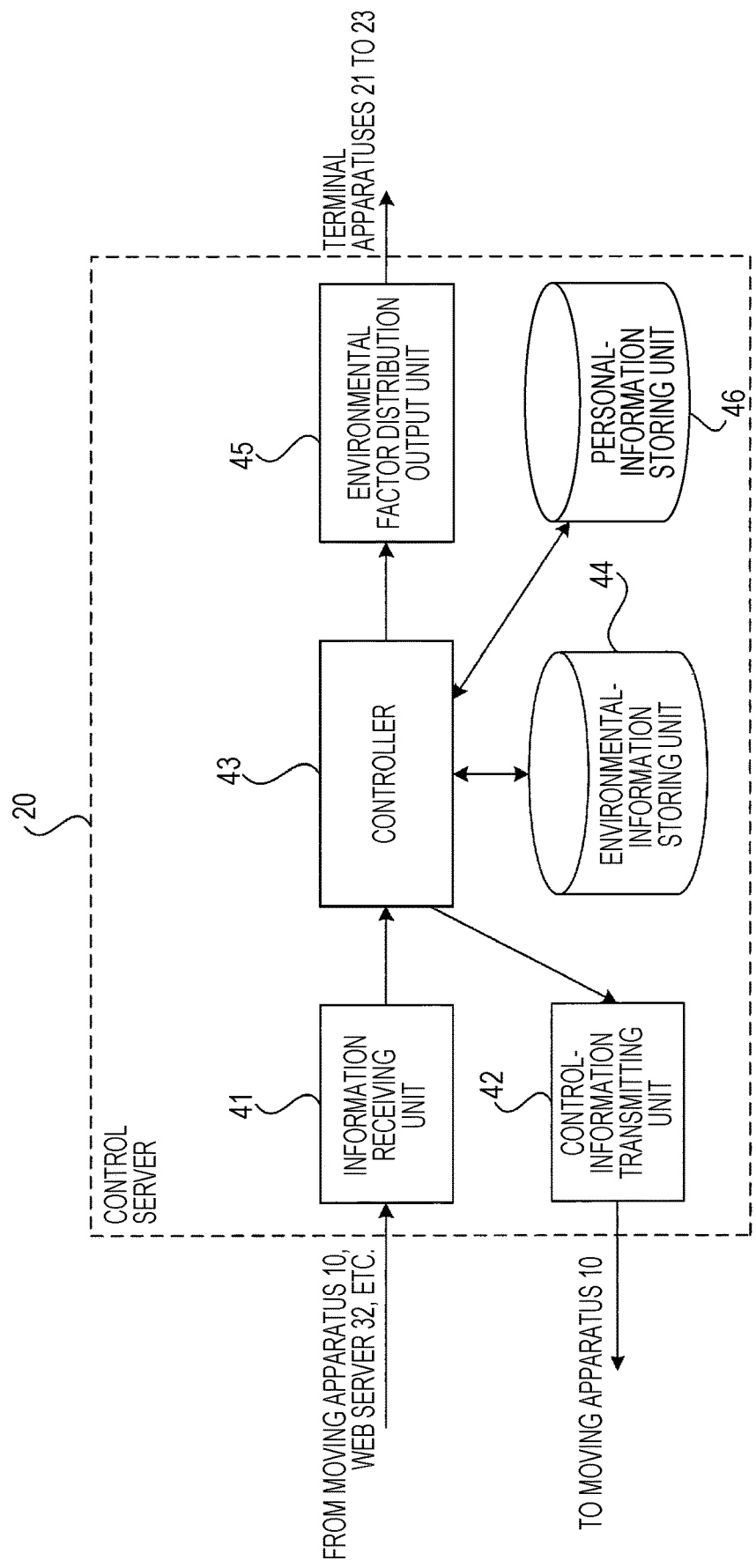
FIG. 4 illustrates a functional configuration of the control server in the environmental measurement system according to the exemplary embodiment of the present invention.

FIG. 4 is a block diagram illustrating a functional configuration of the control server 20 implemented upon the above control programs being executed.

As illustrated in FIG. 4, the control server 20 in the environmental measurement system according to the exemplary embodiment includes an information receiving unit 41, a control-information transmitting unit 42, a controller 43, an environmental-information storing unit 44, an environmental factor distribution output unit 45, and a personal-information storing unit 46.

The information receiving unit 41 receives various kinds of information from the moving apparatus 10 and the web server 32.

The control-information transmitting unit 42 transmits control information for controlling the moving apparatus 10 to the moving apparatus 10 through the wireless LAN terminal 24 under control of the controller 43.

Upon reception of information on environmental factors and other various kinds of sensor information from the moving apparatus 10 through the information receiving unit 41, the controller 43 causes the received information on environmental factors to be stored in the environmental-information storing unit 44 and determines the location of the moving apparatus 10 and controls the movement thereof on the basis of the received sensor information.

In addition, the controller 43 acquires information such as weather forecast information by accessing the web server 32, setting information of an air conditioner installed in the office, and the like.

The environmental-information storing unit 44 stores the information on environmental factors acquired by the controller 43 and information on an environmental factor distribution generated by the controller 43.

Then, on the basis of the information on environmental factors acquired by the moving apparatus 10 and location information of the moving apparatus 10 at the time the information on environmental factors was acquired, the controller 43 calculates an environmental factor distribution in a region in which the moving apparatus 10 moves.

The location information herein is information indicating the location in the region in which the moving apparatus 10 moves, such as a room of an office. The location information is, for example, XYZ coordinates information obtained by setting a certain point in the office as a reference point. In addition, the region in which the moving apparatus 10 moves is a region in which the moving apparatus 10 moves in order to provide a service and is not only the room in the office, but also a shop such as a coffee shop, a restaurant floor, or the like.

The controller 43 controls the movement of the moving apparatus 10 by using the map information, such as the office layout, that has been stored in advance and acquires the location of the moving apparatus 10 in this map information as the location information. Note that the controller 43 may acquire this map information by accessing the web server 32.

As a specific method, the environmental factor distribution is calculated in the following manner.

(1) Acquire map information of a region in which the moving apparatus 10 provides a service.

(2) Store the information on environmental factors acquired by the moving apparatus 10 in association with the location information.

(3) Plot the stored information on environmental factors on locations determined on the basis of each piece of the location information on a map.

(4) Generate distribution information by drawing isothermal lines and the like on the basis of the information on environmental factors plotted on the respective locations on the map.

The environmental factor distribution output unit 45 outputs the environmental factor distribution, calculated by the controller 43, in the region in which the moving apparatus 10 moves.

For example, if the information on environmental factors is temperature information, the environmental factor distribution output unit 45 outputs a temperature distribution in the office. Specifically, the environmental factor distribution output unit 45 outputs the temperature distribution by displaying, on displays of the terminal apparatuses 21 to 23, the temperature distribution obtained by superposing a measured temperature distribution on a map such as an office layout map. Alternatively, the controller 43 may directly display, on a display of the moving apparatus 10, the generated environmental factor distribution.

The personal-information storing unit 46 stores in advance personal information regarding an environmental factor preference of each user. For example, the personal-information storing unit 46 stores personal information that a user is sensitive to heat, cold, airflow from air-conditioners, or the like. This personal information further includes information regarding the age, sex, hometown, and the like of the user.

Figure 5:
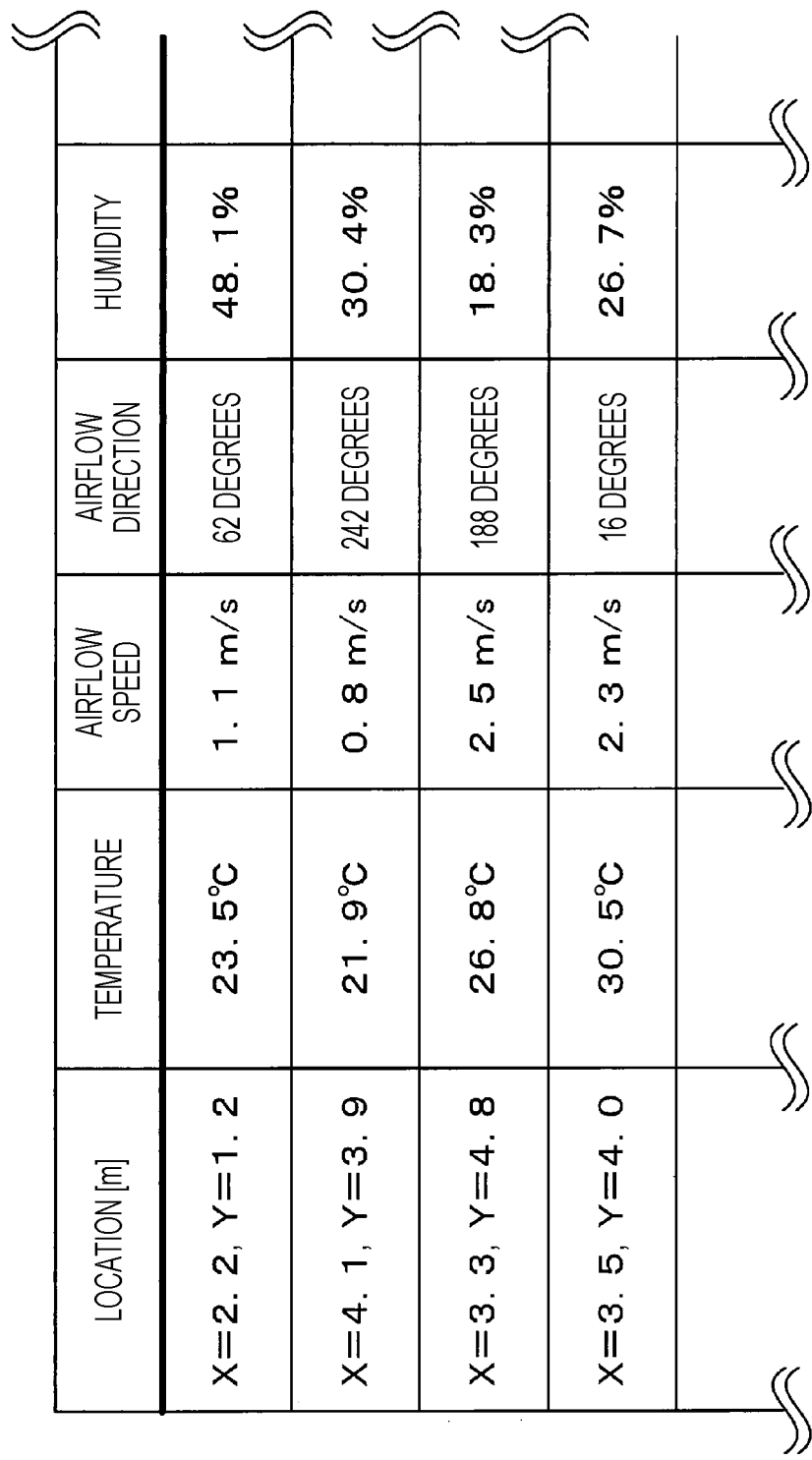
FIG. 5 illustrates exemplary information on environmental factors stored in an environmental-information storing unit.

Now, FIG. 5 illustrates exemplary information on environmental factors stored in the environmental-information storing unit 44.

The exemplary information on environmental factors illustrated in FIG. 5 indicates the information on environmental factors such as the temperature, the airflow speed, the airflow direction, and the humidity according to the location (location information) where the information on environmental factors was acquired.

More specifically, at an initial stage, an open space is measured by using three axes, x, y, and z axes, to set fundamental information. Information to be stored at an initial stage may be two-dimensional information, such as xy- or xz-coordinates, as illustrated in FIG. 5. Calculation of vectors from the xy- or xz-coordinates may produce three-dimensional information at each location. If information in typical xy-regions, as illustrated in FIG. 5, is acquired on a regular basis, by converting the information into xy- and xz-coordinates of other locations on the basis of change information, the latest three-dimensional information may be obtained without measuring all locations.

Figure 6:
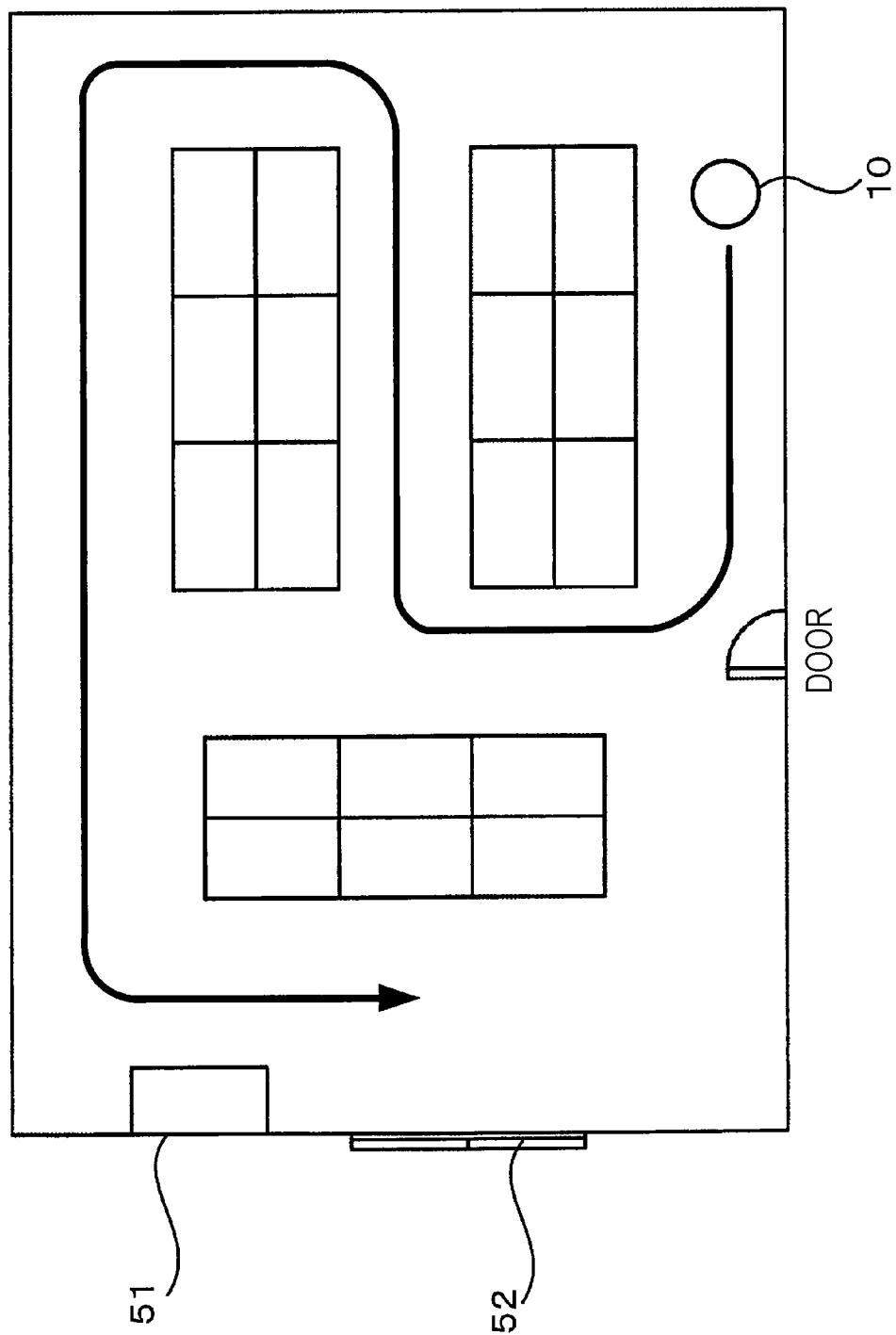
FIG. 6 is an exemplary layout of an office in which the moving apparatus according to the exemplary embodiment of the present invention moves.

Next, FIG. 6 illustrates an exemplary layout of the office in which the moving apparatus 10 according to the exemplary embodiment moves. In the office illustrated in FIG. 6, an air conditioner 51 is installed on a wall, and windows 52 are provided. The moving apparatus 10 autonomously moves in this office.

The moving apparatus 10 moving in the office illustrated in FIG. 6 acquires information on various environmental factors such as the temperature, the humidity, the airflow speed, and the airflow direction at plural locations and transmits, to the control server 20, the acquired information on environmental factors and location information indicating the locations where the information on environmental factors was acquired.

Note that the exemplary embodiment will describe a case in which the environmental factor distribution is displayed by using the environmental measurement system according to the exemplary embodiment in an office where each user's seat is not determined in advance and where the user selects a desired seat on any of screens displayed on the terminal apparatuses 21 to 23.

For example, if temperature information is acquired as the information on environmental factors, by using the temperature information acquired at plural locations in the office, the controller 43 generates a temperature distribution map of the inside of the office. The generated temperature distribution map is output from the environmental factor distribution output unit 45 to the terminal apparatuses 21 to 23 and displayed on the screens.

Figure 7:
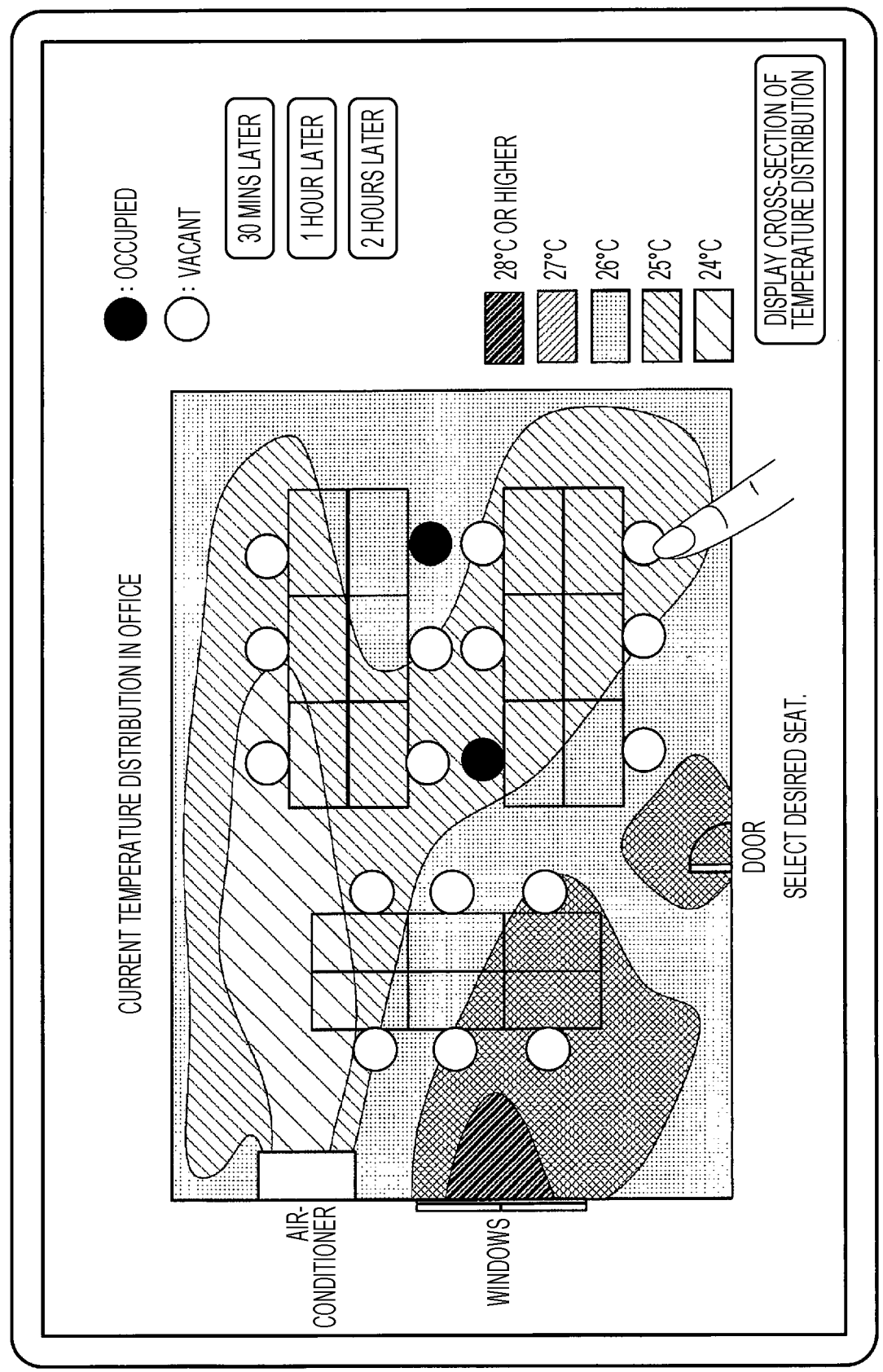
FIG. 7 is an exemplary temperature distribution map that is output from an environmental factor distribution output unit to terminal apparatuses and displayed on screens of the terminal apparatuses.

FIG. 7 illustrates an exemplary temperature distribution map that is displayed in the above manner. In the exemplary display illustrated in FIG. 7, the temperature distribution information in the current office is displayed in different colors according to temperature. This temperature distribution map also displays a message that encourages a user to select a desired seat on this map, and the user is supposed to select their desired seat by referring to the temperature distribution map of the inside of the office.

Upon a desired seat being selected by a user on the displayed temperature distribution map, the controller 43 receives the user's selection. Then, on the display screen, a process is performed in which the seat selected by the user is changed from "vacant" to "occupied".

In the above manner, a user who is sensitive to heat selects a seat at which the temperature is relatively low, thereby taking a seat that matches their preference. In addition, a user who is sensitive to cold selects a seat at which the temperature is relatively high, thereby taking a seat that matches their preference.

Furthermore, on the exemplary display screen illustrated in FIG. 7, a button "display cross-section of temperature distribution" is also displayed. Upon this button being touched by a user, the display screen is switched to a screen illustrated in FIG. 8, for example.

Figure 8:
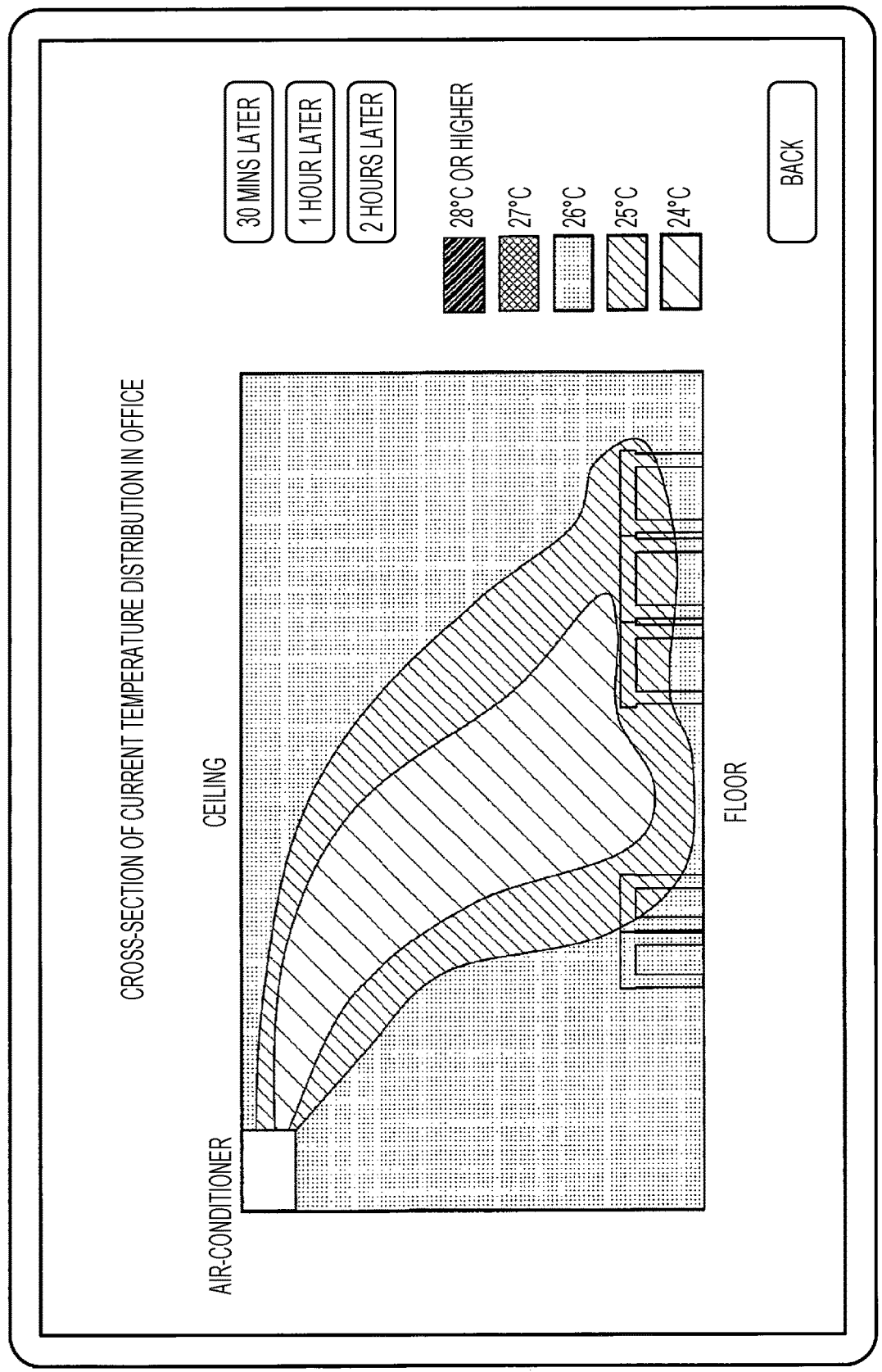
FIG. 8 illustrates a display example of a cross-sectional view of a temperature distribution map that is output from the environmental factor distribution output unit to the terminal apparatuses and displayed on the screens of the terminal apparatuses.

The exemplary display screen illustrated in FIG. 8 is a cross-sectional view of the temperature distribution in the office, by which a user may understand the temperature distribution in consideration of the vertical direction.

Note that FIG. 7 and FIG. 8 each illustrate a case in which information indicating the temperature distribution in the office is displayed on the terminal apparatuses 21 to 23. In contrast, FIG. 9 and FIG. 10 each illustrate an exemplary case in which information indicating an air volume distribution (airflow speed and airflow direction) is displayed by being superposed on the temperature distribution. Note that the direction of each arrow represents the airflow direction, and the size of the arrow represents the airflow speed in FIG. 9 and FIG. 10.

Figure 9:
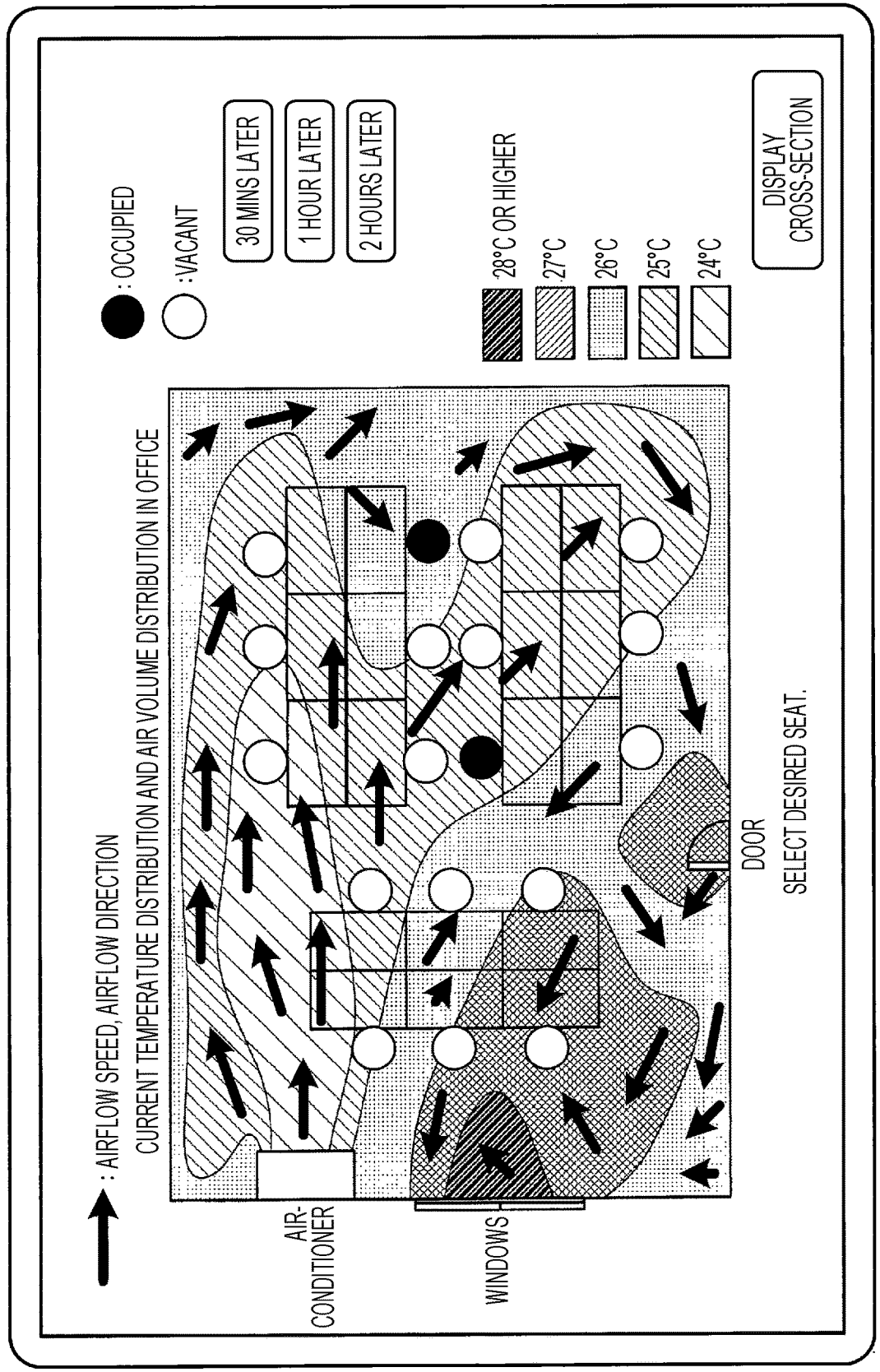
FIG. 9 illustrates an exemplary environmental factor distribution map representing two-dimensional temperature and air volume distributions in the office.
Figure 10:
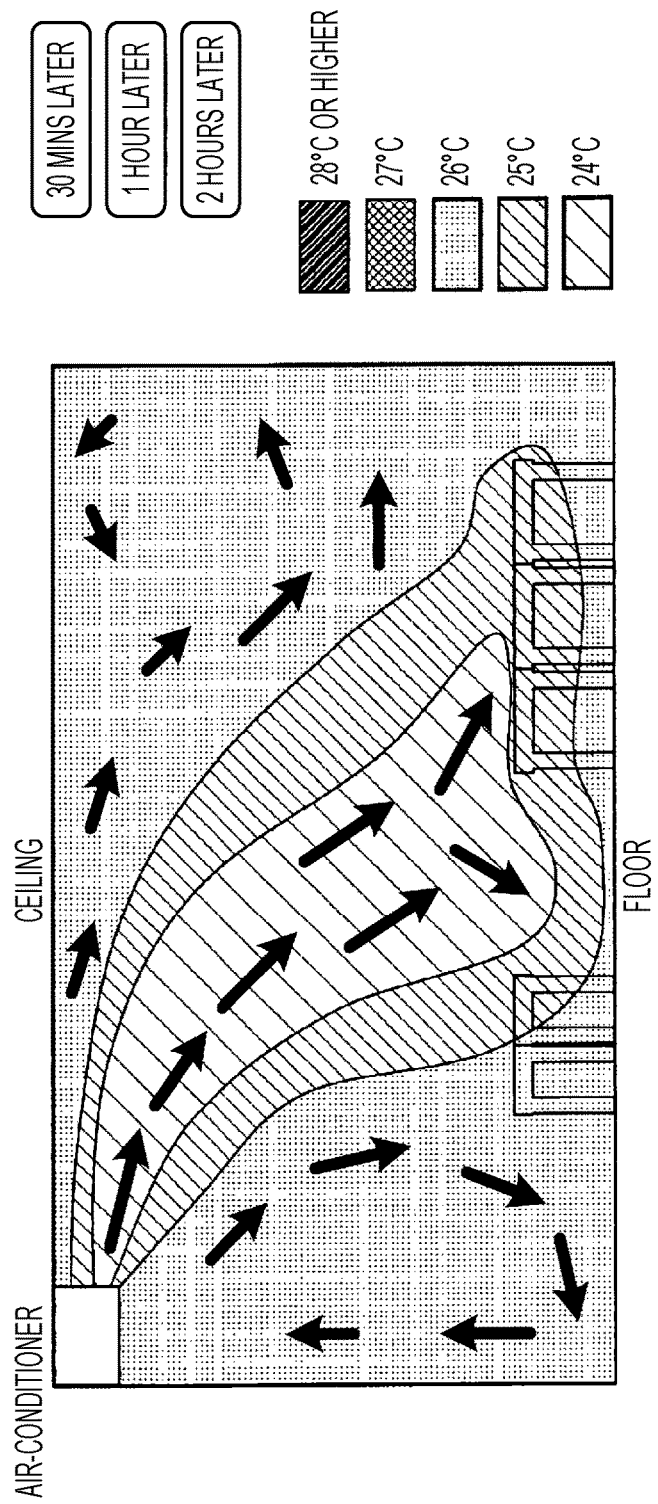
FIG. 10 illustrates an exemplary environmental factor distribution map representing three-dimensional temperature and air volume distributions in the office.

FIG. 9 illustrates an exemplary environmental factor distribution map indicating two-dimensional temperature and air volume distributions in the office. FIG. 10 illustrates an exemplary environmental factor distribution map indicating three-dimensional temperature and air volume distributions in the office.

Note that instead of a user selecting a desired seat, the controller 43 may select a seat that matches the user's preference on the basis of the environmental factor distribution that has been output from the environmental factor distribution output unit 45 and the personal information stored in the personal-information storing unit 46 so as to guide the user to the selected seat.

For example, the controller 43 selects a seat at a relatively high temperature for a user who is likely to prefer a high temperature, such as a user who is sensitive to cold, an elderly user, or a female user, according to the personal information that has been registered in advance, and guides such a user to the selected seat. Specifically, the controller 43 selects a seat included in a region at the highest temperature in the temperature distribution for a user who is likely to prefer a high temperature and guides the user to the selected seat. Alternatively, the controller 43 selects a seat included in a region at a preset temperature, for example, 28° C. or higher, in the temperature distribution, for a user who is likely to prefer a high temperature and guides the user to the selected seat.

In contrast, the controller 43 selects a seat at a relatively low temperature for a user who is likely to prefer a low temperature, such as a user who is sensitive to heat, a young user, an obese user, or a male user, according to the personal information that has been registered in advance, and guides such a user to the selected seat. Specifically, the controller 43 selects a seat included in a region at the lowest temperature in the temperature distribution for a user who is likely to prefer a low temperature and guides the user to the selected seat. Alternatively, the controller 43 selects a seat included in a region at a preset temperature, for example, 27° C. or lower, in the temperature distribution, for a user who is likely to prefer a low temperature and guides the user to the selected seat.

Specifically, a user is instructed to follow the moving apparatus 10, and the moving apparatus 10 is controlled to move to the vicinity of the selected seat so as to guide the user to the selected seat. In addition, for example, only the selected seat may be displayed with a spotlight, lighting of the selected seat may blink, or a lighting color of the selected seat may be changed to be different from the lighting color of the other seats, so as to guide the user.

Note that the temperature distribution and the like in the office change over time. Thus, even if a user takes a seat that matches their preference, the seat may no longer match their preference in the future.

Accordingly, the controller 43 may not only calculate the current environmental factor distribution, but also may estimate a future change in the environmental factor distribution in the office on the basis of current date-and-time information, weather forecast information, setting information of an air conditioner, structural information of the office, or history information of an environmental factor distribution in the office in the past, alone or in combination.

For example, the controller 43 acquires the current date-and-time information, and in consideration of the current date and time, the season, the incident angle of sunlight, and the like, the controller 43 estimates a future change in the temperature. In addition, by accessing the web server 32 or the like, the controller 43 acquires the weather forecast information of each hour of the day, and in consideration of the acquired weather forecast information, the controller 43 estimates a future change in the temperature.

In addition, in consideration of set-temperature information of an air conditioner and the structural information of the office, such as the location of doors, the location of windows, or the installation location of the air conditioner, the controller 43 estimates a future change in the temperature.

Furthermore, on the basis of the history information such as temperature distribution maps in the past, by referring to a temperature distribution map of the past in which the conditions are similar to the current conditions, the controller 43 estimates a future change in the temperature.

Subsequently, the environmental factor distribution output unit 45 outputs the future environmental factor distribution estimated by the controller 43.

Figure 11:
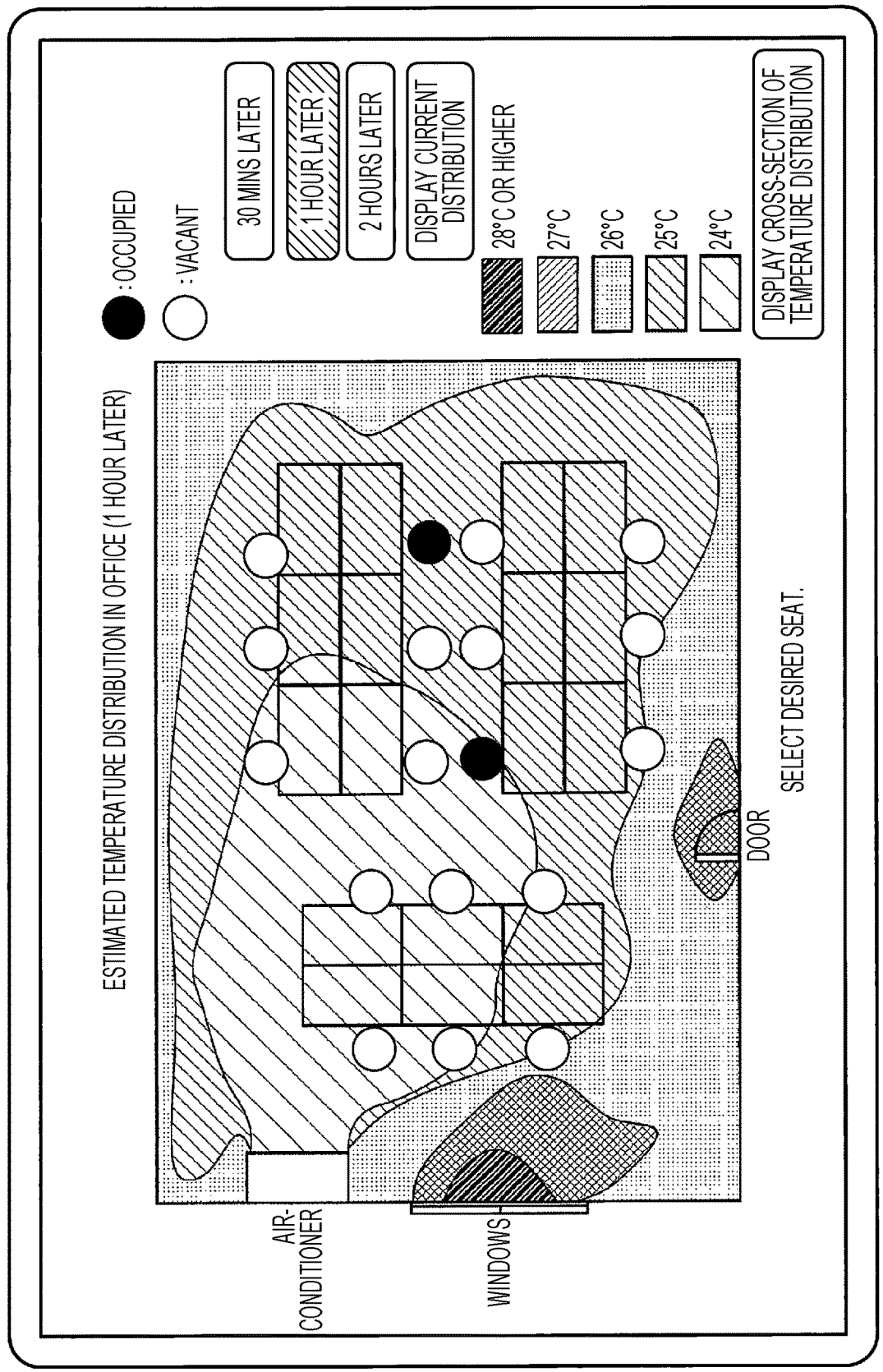
FIG. 11 illustrates a display example of a 1-hour-later temperature distribution map of the inside of the office.

For example, upon a button "1 hour later" on the exemplary display screen illustrated in FIG. 7 being touched by a user, the display screen is switched to a display screen illustrated in FIG. 11, for example, and the user may check a 1-hour-later temperature distribution. Thus, the user may select a desired seat in consideration of a future change in the temperature distribution. That is, a user who prefers a low temperature may select a seat at which the temperature will not rise in an hour among seats at which the temperature is relatively low at the moment.

A user may select and reserve a seat by checking such a 1-hour-later temperature distribution. If a seat is thus reserved, this seat is no longer reservable by another user. In addition, if a user who has already reserved a seat selects another vacant seat, the reservation of the former seat is cancelled, and this seat becomes reservable by another user. That is, one seat is set as reservable by each user who is identified on the basis of the personal information.

If the moving apparatus 10 provides a service of selling goods, the controller 43 may control a destination and a route of the moving apparatus 10 at the time of selling goods by using the moving apparatus 10 on the basis of the environmental factor distribution that has been output from the environmental factor distribution output unit 45.

For example, as illustrated in FIG. 12, in a case of selling coffee by using the moving apparatus 10, on the basis of an air volume distribution map that has been output from the environmental factor distribution output unit 45, the controller 43 causes the moving apparatus 10 to wait at the upstream of a user 60 who often buys a coffee so that the flavor of coffee is delivered to the user 60. Thus, the user 60 is expected to buy a coffee, influenced by the flavor of coffee.

The moving apparatus 10 may acquire information on environmental factors while moving in order to provide a service.

Further, the control server 20 may control an air-conditioner installed in the office, window shades (light-shielding unit), light transmittance of window glass, lighting equipment, and the like, so as to actively change the environment of the office to a desired state.

For example, the control server 20 controls the set temperature (target temperature), target humidity, airflow direction setting, air volume setting, operation mode, such as cooling, heating, dehumidifying, of the air conditioner, so as to adjust the temperature, the humidity, the air volume, and the like in the office. In addition, the control server 20 may adjust the light intensity of lighting equipment in the office, may control incident light by using window shades, or may adjust the light intensity by changing the transmittance of window glass, so as to control a light intensity distribution. Note that the incident light may be controlled by using window shades, or the transmittance of window glass may be changed, so as to control the temperature near windows.

Specifically, the controller 43 may control environment adjusting facilities such as an air-conditioner and window shades installed in the office in such a manner that the environmental factor distribution that has been output from the environmental factor distribution output unit 45 becomes closer to a preset distribution.

The controller 43 may control the environment adjusting facilities installed in the office in such a manner that the environmental factor distribution in the office becomes more uniform regardless of location. For example, the controller 43 may control the environment adjusting facilities such as an air-conditioner and window shades in such a manner that temperature differences depending on the location are reduced in the temperature distribution in the office. In addition, the controller 43 may adjust the air volume and airflow direction of an air conditioner in such a manner that air volume differences are reduced in an air volume distribution in the office.

Note that the exemplary embodiment has mainly described above a case in which the temperature and air volume distributions in the office are measured and displayed. However, another environmental factor distribution map, such as a humidity distribution map, a noise distribution map, or a light-intensity distribution map, may be generated and displayed.

Modification

The above exemplary embodiment has described a case of generating an environmental factor distribution map such as the temperature distribution map of the inside of the office. However, the present invention is not limited to this case. The exemplary embodiment of the present invention is also applicable to a case of generating an environmental factor distribution map of any of a variety of regions such as public facilities including libraries, restaurants, coffee shops, and manga café s. In such a case, the controller 43 automatically acquires and generates a map of the region such as a restaurant, a coffee shop, or a manga café by searching the web server 32 related to the corresponding facility. Note that the map of the region may be stored in the storage device 13 or the like in advance and may be acquired therefrom.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An environmental measurement system comprising:
    a moving apparatus including an acquiring unit that acquires information on environmental factors, the moving apparatus being capable of autonomously moving in a predefined region, the moving apparatus including a laser sensor configured to obtain information regarding shapes of surrounding objects, the moving apparatus configured to move along a floor of a room having the predefined region;
    an output unit that outputs an environmental factor distribution in the region, the environmental factor distribution having been calculated on the basis of the information on environmental factors acquired by the moving apparatus and location information of the moving apparatus at the time the information on environmental factors was acquired, the location information being determined by combining (a) the information regarding shapes of surrounding objects obtained by the laser sensor and (b) stored map information;
    a storing unit in which personal information regarding an environmental factor preference of each user is stored in advance; and
    a guiding unit that guides a user to choose a particular seat in the room on the basis of the environmental factor distribution that has been output from the output unit and the personal information that is stored in the storing unit.

2. The environmental measurement system according to claim 1,
    wherein the information on environmental factors is temperature information, and
    wherein the output unit outputs a temperature distribution in the region.

3. The environmental measurement system according to claim 2,
    wherein the output unit outputs the temperature distribution by displaying the temperature distribution on a display, and
    wherein the environmental measurement system further comprises a reception unit that receives a selection of a desired seat in the displayed temperature distribution.

4. The environmental measurement system according to claim 1, further comprising:
    an estimating unit that estimates a future change in the environmental factor distribution in the region on the basis of current date-and-time information, weather forecast information, setting information of an air conditioner, structural information of the region, or history information of an environmental factor distribution in the region in a past, alone or in combination,
    wherein the output unit outputs a future environmental factor distribution estimated by the estimating unit.

5. The environmental measurement system according to claim 1, wherein the acquiring unit acquires, as the information on environmental factors, airflow direction and airflow speed information in an open space on the basis of a direction and a speed of movement of fine substances in the open space detected by radiating a laser of the laser sensor into the open space.

6. The environmental measurement system according to claim 1, further comprising:
    a controller that controls a destination and a route of the moving apparatus at a time of selling goods by using the moving apparatus on the basis of the environmental factor distribution that has been output from the output unit.

7. The environmental measurement system according to claim 1, further comprising:
    a controller that controls environment adjusting facilities installed in the region in such a manner that the environmental factor distribution that has been output from the output unit becomes closer to a preset distribution.

8. The environmental measurement system according to claim 7, wherein the controller further controls the environment adjusting facilities installed in the region in such a manner that the environmental factor distribution in the region becomes more uniform regardless of location.

9. The environmental measurement system according to claim 1, wherein the acquiring unit comprises an odor sensor that acquires the information on the environmental factors.

10. An environmental measurement system comprising:
a controller that performs control to output an environmental factor distribution in a predefined region to an output unit, the environmental factor distribution having been calculated on the basis of information on environmental factors acquired by a moving apparatus that is capable of autonomously moving in the region and location information of the moving apparatus at the time the information on environmental factors was acquired, the moving apparatus including a laser sensor configured to obtain information regarding shapes of surrounding objects, the moving apparatus configured to move along a floor of a room having the predefined region, the location information being determined by combining (a) the information regarding shapes of surrounding objects obtained by the laser sensor and (b) stored map information; and
a storing unit in which personal information regarding an environmental factor preference of each user is stored in advance; and
wherein the controller further guides a user to choose a particular seat in the room on the basis of the output environmental factor distribution and the personal information that is stored in the storing unit.

11. A non-transitory computer readable medium storing a program causing a computer to execute a process for environmental measurement, the process comprising:
outputting an environmental factor distribution in a predefined region to an output unit, the environmental factor distribution having been calculated on the basis of information on environmental factors acquired by a moving apparatus that is capable of autonomously moving in the region and location information of the moving apparatus at the time the information on environmental factors was acquired, the moving apparatus including a laser sensor configured to obtain information regarding shapes of surrounding objects, the moving apparatus configured to move along a floor of a room having the predefined region, the location information being determined by combining (a) the information regarding shapes of surrounding objects obtained by the laser sensor and (b) stored map information;
storing personal information regarding an environmental factor preference of each user; and
guiding a user to choose a particular seat in the room on the basis of the output environmental factor distribution and the stored personal information.

* * * * *